US005359039A

United States Patent [19]

Smith et al.

[11] Patent Number: 5,359,039

[45] Date of Patent: Oct. 25, 1994

[54] ISOLATED POXVIRUS A53R-EQUIVALENT TUMOR NECROSIS FACTOR ANTAGONISTS

[75] Inventors: Craig A. Smith; Raymond G. Goodwin, both of Seattle, Wash.

[73] Assignee: Immunex Corporation, Seattle, Wash.

[21] Appl. No.: 89,458

[22] Filed: Jul. 9, 1993

[51] Int. Cl.[5] ........................ C07K 13/00; C07K 15/04

[52] U.S. Cl. .................................... 530/350; 530/826; 424/186.1; 424/232.1; 536/23.72; 930/220

[58] Field of Search ........................ 424/89; 536/23.72; 530/350, 826, 412; 930/220; 514/12

[56] References Cited

U.S. PATENT DOCUMENTS 5,075,236 12/1991 Yone et al. .......................... 436/518

OTHER PUBLICATIONS

McFadden, G. in *Virus Diseases in Laboratory and Captive Animals;* Darai, G. (ed), Martinus Nijoff, Publishers, Boston; pp. 37-61 (1988).

Horton et al., *J. Virol.* 65:2629-2639; 1991.

Goodwin and Smith, in: *Contributions to Cellular and Molecular Endocrinology* Henry and Norman (eds); University of California, Riverside; pp. 43-48; 1991.

Goebel et al., *Virology* 179:247-266; 1990.

Pickup et al., *Proc. Natl. Acad. Sci. USA* 81:6817-6821; 1984.

Smith et al., "T2 Open Reading Frame from the Shope Fibroma Virus . . . " *Biochem. Biophys. Res. Comm.* 176(1):335-342 (Apr. 1991).

Howard et al., "Vaccinia Virus . . . ORF Related to the Tumor Necrosis Factor Receptor Family", *Virol.* 180:633-647 (Feb. 1991).

Upton et al., "Myxoma Virus Expresses a Secreted Protein . . . " *Virol.* 184:370-382 (Sep. 1991).

Sprang et al., "The divergent receptors for TNF" *TIBS* 15:366-368 (Oct. 1990).

Kohno et al., "A second tumor necrosis factor receptor gene . . . " *PNA* 87:8331-8335 (Nov. 1990).

Upton et al., "Tumorigenie Poxviruses: Genomic Organization . . . " Virol. 160:20-30 (Sep. 1987).

Smith et al., "A Receptor for Tumor Necrosis Factor Defines an Unusual Family of Cellular and Viral Proteins" *Science* 248:1019-1023 (May 1990).

Traktman, "Poxviruses: An Emerging Portrait of Biological Strategy", *Cell* 62:621-626 (Aug. 1990).

*Primary Examiner*—Stephen G. Walsh
*Attorney, Agent, or Firm*—Patricia Anne Perkins; Scott G. Hallquist; Christopher L. Wight

[57] ABSTRACT

Isolated viral proteins, and pharmaceutical compositions made therefrom, are disclosed which are capable of binding to Tumor Necrosis Factor, thereby functioning as Tumor Necrosis Factor antagonists. Also disclosed are processes for preparing isolated viral protein cytokine antagonists.

2 Claims, No Drawings

ISOLATED POXVIRUS A53R-EQUIVALENT TUMOR NECROSIS FACTOR ANTAGONISTS

BACKGROUND OF THE INVENTION

The present invention relates generally to the field of viral proteins, and more specifically to vital proteins having immunoregulatory activity.

The immune system protects an organism from infection and disease through the interaction of specialized white blood cells which recognize and destroy invading microbes and diseased cells. The specialized white blood cells are controlled and coordinated by specific proteins known as cytokines, which direct the development, proliferation, function and effectiveness of these cells. Cytokines act upon immune cells by binding specific proteins, called cytokine receptors, which are located on immune cell surfaces.

The immune response can be modulated by cytokine antagonists, which act by binding cytokines, and preventing the cytokines from binding their respective receptors. Pathogenic organisms may make use of such cytokine antagonists to modulate an infected organism's immune response. Certain viruses are exemplary of such pathogens; the genetic material of such viruses encodes proteins which are similar to certain mammalian cytokine receptors, and which bind to a cytokine and prevent that cytokine from exerting an effect upon an immune cell.

Poxviruses are large, structurally-complex, DNA-containing viruses. Within the Poxviridae family, the subfamily Chordopoxvirinae comprises six genera of poxviruses, including Othopoxvirus, Leporipoxvirus and Avipoxvirus. Vaccinia virus (VV), an Orthopoxvirus, is considered the prototypic poxvirus; significant strides have been made in understanding the molecular biology of poxviruses by studying VV (reviewed in P. Traktman, *Cell* 62:621–626; 1990).

The entire sequence of the Copenhagen strain of vaccinia virus has been published (Paoletti et al., *Virology* 179:247–266, 1990). The Copenhagen sequence predicts 198 open reading frames (ORFs) of at least 60 amino acids. Howard et al. (*Virology* 180:633–647; 1990) report the structure of nine ORFs from the right-hand inverted terminal repeat (ITR) of the WR strain of vaccinia virus. Very few ORFs have been identified as encoding specific viral proteins.

The present invention identifies a specific class of poxvirus proteins having immunosuppressive activity, and provides a method for identifying and isolating such viral proteins. The invention also provides pharmaceutical compositions for regulating immune responses.

SUMMARY OF THE INVENTION

The present invention provides isolated vital proteins having cytokine antagonist activity, and pharmaceutical compositions comprising such viral proteins for regulating immune responses. The present invention also provides processes for preparing isolated viral proteins having cytokine antagonist activity.

The isolated viral proteins of this invention are similar to cytokine binding proteins, such as the extracellular region of a cytokine receptor, and are capable of binding a cytokine and preventing the cytokine from binding to its receptor. The ability of such viral proteins to mimic the activity of a cytokine receptor (and thereby downregulate specific immune responses) enables the viral protein to circumvent the anti-viral defense mechanisms of the host organisms and confers a selective advantage to the virus. The viral proteins of the present invention can be used to regulate immune responses in a therapeutic setting.

The present invention specifically provides isolated Cowpox virus (CPV) A53R-equivalent protein, which is an expression product of the CPV A53R-equivalent open reading frame, and has Tumor Necrosis Factor (TNF) antagonist activity. A53R is an ORF from the right-hand inverted terminal repeat (ITR) of VV; an exemplary vital TNF-binding protein is encoded by the equivalent ORF of CPV.

These and other aspects of the present invention will become evident upon reference to the following detailed description of the invention.

DETAILED DESCRIPTION OF THE INVENTION

The present invention relates to viral proteins which are capable of modulating the activity of cytokines by acting as cytokine antagonists. Proteins encoded by the T2 ORF of several different poxviruses, including both Orthopox and Leporipox viruses, bear amino acid sequence similarity to the ligand-binding region of Tumor Necrosis Factor (TNF) receptor (e.g., the extracellular region of the receptor; TNFR) or to a soluble TNFR and are capable of binding to TNF and preventing the cytokine from binding to TNFR (U.S. patent application No. 07/963,330, filed Oct. 19, 1992, now pending the disclosure of which is incorporated by reference herein). TNFR comprises two polypeptides, p60 and p80, both of which are members of the TNFR family (Smith et al., *Science* 248:1019–1023; 1990). A hallmark of the TNF family of receptors is the presence of several cysteine-rich domains. A second CPV protein encoded by a different ORF, the A53R-equivalent ORF, also exhibits a certain degree of similarity to TNFR, as well as to other members of the TNF family, including T2 proteins, 4-1BB, OX40, nerve growth factor (NGF) and CD40. The protein encoded by CPV A53R-equivalent binds TNF and inhibits binding of TNF to TNFR.

The deduced translation product of A53R ORF of VV (described in Howard et al.; also referred to as SalF19R) has a molecular weight of 12 Kda, and, similar to the members of the TNFR family contains a high proportion of cysteine residues. However. the ORF contains a termination codon that precludes translation of a polypeptide containing more than one cysteine-rich domain. In contrast, the A53R-equivalent ORF of CPV does not contain a premature termination codon. Expression of the A53R-equivalent CPV ORF in mammalian cells results in a polypeptide of approximately 18 Kd, which contains four cysteine-rich domains, and binds TNF. An A53R-equivalent ORF is present in many other members of the poxvirus family. The ORF bears significant similarity to genes encoding other members of the TNF family; upon expression, full-length A53R-equivalent ORF gene products will bind TNF.

Definitions

As used herein, the term "viral protein" refers to proteins encoded by RNA, DNA, mRNA or cDNA isolated or otherwise derived from a viral source.

"Isolated", as used in the context of the present invention to define the purity of viral proteins, refers to proteins which are substantially free of other human or viral proteins of natural or endogenous origin and contains less than about 1% by mass of protein contaminants residual of production processes. Such compositions, however, can contain other proteins added as stabilizers, carriers, excipients or co-therapeutics. Isolated viral proteins are detectable as a single protein band in a polyacrylamide gel by silver staining.

A "cytokine" is a specific protein which directs the development, proliferation, function and effectiveness of cells of the immune system. Specific examples of "cytokines" include, but are not limited to, the interleukins (e.g., IL-1, IL-2, IL-3, IL-4, IL-5, IL-6, IL-7, IL-8, IL-9, IL-10, IL-11, IL-12), interferon (IFNα and IFNβ), tumor necrosis factor (TNFα and TNFβ) and various growth factors, such as GM-CSF, G-CSF, and CSF-1. Each of the above cytokines transduces a biological signal by binding to a receptor molecule specific to the cytokine.

A vital protein having "cytokine antagonist activity" inhibits, counteracts or neutralizes the biological activity of a cytokine. Cytokine antagonist activity may be effected by means of the vital protein sterically hindering the binding of a cytokine to its receptor, thereby preventing cytokine signal transduction. For example, a viral protein can sterically hinder the binding of a cytokine to its receptor by binding the cytokine or its receptor at or near a site required for cytokine/receptor binding. The viral protein thus physically prevents the cytokine and receptor from interacting and transducing a biological signal. Specific examples of vital proteins having cytokine antagonist activity include polypeptides encoded by the T2 ORF of poxviruses, including Shope Fibroma virus (SFV), myxoma virus and CPV. The DNA sequence of the T2 ORF and the amino acid sequence of T2 for SFV, myxoma and CPV are set forth in U.S. application Ser. No. 07/963,330, filed Oct. 19, 1992, now pending which is incorporated by reference herein. Additional examples of viral TNF-binding proteins include proteins encoded by A53R-equivalent genes of poxviruses, as disclosed herein.

Tumor necrosis factor-α (TNFα, also known as cachectin) and tumor necrosis factor-β (TNF-β, also known as lymphotoxin) are homologous mammalian endogenous secretory proteins capable of inducing a wide variety of effects on a large number of cell types. The great similarities in the structural and functional characteristics of these two cytokines have resulted in their collective description as "TNF." Complementary DNA clones encoding TNFα (Pennica et al., *Nature* 312:724, 1984) and TNFβ (Gray et al., *Nature* 312:721, 1984) have been isolated.

TNF initiates its biological effect on cells by binding to specific TNFR expressed on the plasma membrane of a TNF-responsive cell. It is believed that TNFα and TNFβ share a common receptor. The proteins encoded by the T2 ORF are TNF antagonists that act by binding to TNF and inhibiting binding of TNF to TNFR. Although unrelated to the T2 ORF, the A53R-equivalent ORF also encodes protein that binds TNF and inhibits binding of TNF to TNFR. Thus, A53R-equivalent protein compositions will be useful in diagnostic assays for TNF, as well as in raising antibodies to A53R-equivalent protein for use in diagnosis and therapy. In addition, purified A53R-equivalent protein compositions may be used directly in therapy to bind or scavenge TNF, thereby providing a means for regulating the immune activities of TNF. In order to study the structural and biological characteristics of A53R-equivalent protein and the roles played by A53R-equivalent protein in the responses of various cell populations to viral infection by poxviruses, or to use A53R-equivalent protein effectively in therapy, diagnosis, or assay, purified compositions of A53R-equivalent protein are needed. Such compositions, are obtainable in practical yields by cloning and expressing genes encoding the receptors using recombinant DNA technology.

The terms "TNF receptor" and "TNFR" refer to proteins having amino acid sequences of the native mammalian TNF receptor amino acid sequences.

A "soluble cytokine receptor", as used in the context of the present invention, refers to a protein, or a substantially equivalent analog, having an amino acid sequence corresponding to the extracellular region of a native cytokine receptor, for example polypeptides having the amino acid sequences substantially equivalent to the extracellular region of TNF receptor. Because soluble proteins are devoid of a transmembrane region, they are secreted from the host cell in which they are produced. Viral proteins having an amino acid sequence and/or structure sufficiently similar to the extracellular region of a cytokine receptor or to a soluble cytokine receptor will retain the ability to bind the cytokine and inhibit the ability of the cytokine to transduce a signal via cell surface bound cytokine receptor proteins. When administered in therapeutic formulations, the viral proteins circulate in the body and bind to circulating cytokine molecules, preventing interaction of the cytokine with natural cytokine receptors and inhibiting transduction of cytokine-mediated biological signals, such as immune or inflammatory responses.

A viral protein has "cytokine antagonist activity" if the viral protein has a sequence of amino acids or structure "sufficiently similar" to either the extracellular region of a cytokine receptor or to a soluble receptor that the viral protein is capable of inhibiting binding of the cytokine receptor to its ligand, thereby inhibiting cytokine signal transduction. Assays for determining cytokine binding inhibition are described below in Example 1. Inhibition of cytokine signal transduction can be determined by transfecting cells with recombinant cytokine receptor DNAs to obtain recombinant receptor expression. The cells are then contacted with the cytokine ligand and the resulting metabolic effects examined. If an effect results which is attributable to the action of the ligand, then the recombinant receptor has signal transducing activity. Exemplary procedures for determining whether a polypeptide has signal transducing activity are disclosed by Idzerda et al., *J. Exp. Med.* 171:861 (1990); Curtis et al., *Proc. Natl. Acad. Sci. USA* 86:3045 (1989); Prywes et al., *EMBO J.* 5:2179 (1986); and Chou et al., *J. Biol. Chem.* 262:1842 (1987). Alternatively, primary cells of cell lines which express an endogenous cytokine receptor and have a detectable biological response to the cytokine could also be utilized. Such procedures are used as controls for assaying inhibition of signal transduction by the viral protein cytokine antagonists of the present invention.

"Recombinant," as used herein, means that a protein is derived from recombinant (e.g., microbial or mammalian) expression systems. "Microbial" refers to recombinant proteins made in bacterial or fungal (e.g., yeast) expression systems. As a product, "recombinant microbial" defines a protein produced in a microbial expression system which is essentially free of native endogenous substances. Protein expressed in most bacterial cultures, e.g., *E. coli,* will be free of glycan. Protein expressed in yeast may have a glycosylation pattern different from that expressed in mammalian cells.

"Biologically active," as used throughout the specification as a characteristic of a cytokine or a cytokine receptor, means that a particular molecule shares sufficient amino acid sequence similarity with the cytokine or receptor to be capable of binding detectable quantities of the cytokine, or cross-reacting with anti-cytokine receptor antibodies raised against the cytokine from natural (i.e., nonrecombinant) sources.

"DNA sequence" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the sequence and its component nucleotide sequences by standard biochemical methods, for example, using a cloning vector. Such sequences are preferably provided in the form of an open reading frame uninterrupted by internal nontranslated sequences, or introns, which are typically present in eukaryotic genes. Genomic DNA containing the relevant sequences could also be used. Sequences of non-translated DNA may be present 5' or 3' from the open reading frame, where the same do not interfere with manipulation or expression of the coding regions.

The viral proteins of the present invention having cytokine antagonist activity are identified by isolating and then analyzing a viral protein, RNA, DNA, mRNA or cDNA to provide an amino acid sequence of the vital protein. The amino acid sequence of the viral protein is then compared with the amino acid sequence of a cytokine or cytokine receptor. Those viral proteins can be selected and isolated which prevent the cytokine from binding its receptor, or which have a sequence similar to a cytokine and are capable of binding to a cytokine receptor (without transducing a cytokine signal) and inhibiting binding of the cytokine to its receptor.

Alternative methods for identifying viral proteins having cytokine antagonist activity include selecting a vital RNA, DNA, mRNA or cDNA capable of hybridization under moderately stringent conditions to DNA or cDNA clones encoding a cytokine binding protein, and isolating the protein. Moderate stringency hybridization conditions refer to conditions described in, for example, Sambrook et al. *Molecular Cloning: A Laboratory Manual,* 2 ed. Vol. 1, pp. 1.101–104, Cold Spring Harbor Laboratory Press, (1989). Conditions of moderate stringency, as defined by Sambrook et al., include use of a prewashing solution of 5× SSC, 0.5% SDS, 1.0 mM EDTA (pH 8.0) and hybridization conditions of 50° C., 5× SSC, overnight. Conditions of severe stringency include higher temperatures of hybridization and washing. Those DNA or RNA sequences capable of hybridization to DNA clones encoding a cytokine binding protein under such conditions can be selected and which encode proteins that have a sequence similar to a cytokine and are capable of binding to a cytokine receptor (without transducing a cytokine signal) and inhibiting binding of the cytokine to its receptor, can then be selected, and the protein encoded thereby isolated.

Proteins and Analogs

The present invention provides isolated proteins having cytokine antagonist activity. Such proteins are substantially free of contaminating endogenous materials and, optionally, without associated native-pattern glycosylation. Derivatives of the vital proteins within the scope of the invention also include various structural forms of the primary protein which retain biological activity. Due to the presence of ionizable amino and carboxyl groups, for example, a protein n-my be in the form of acidic or basic salts, or may be in neutral form. Individual amino acid residues may also be modified by oxidation or reduction.

The primary amino acid structure may be modified by forming covalent or aggregative conjugates with other chemical moieties, such as glycosyl groups, lipids, phosphate, acetyl groups and the like, or by creating amino acid sequence mutants. Covalent derivatives are prepared by linking particular functional groups to amino acid side chains or at the N- or C-termini.

Other derivatives of the protein within the scope of this invention include covalent or aggregative conjugates of the protein or its fragments with other proteins or polypeptides, such as by synthesis in recombinant culture as N-terminal or C-terminal fusions. For example, the conjugated peptide may be a signal (or leader) polypeptide sequence at the N-terminal region of the protein which co-translationally or post-translationally directs transfer of the protein from its site of synthesis to its site of function inside or outside of the cell membrane or wall (e.g., the yeast α-factor leader). Protein fusions can comprise peptides added to facilitate purification or identification of viral proteins (e.g., poly-His). The amino acid sequence of the viral proteins can also be linked to a peptide such as that described by Hopp et al., *Bio/Technology* 6:1204 (1988). Such a highly antigenic peptide provides an epitope reversibly bound by a specific monoclonal antibody, enabling rapid assay and facile purification of expressed recombinant protein. The sequence of Hopp et al. is also specifically cleaved by bovine mucosal enterokinase, allowing removal of the peptide from the purified protein. Fusion proteins capped with such peptides may also be resistant to intracellular degradation in *E. coli.* Fusion proteins further comprise the amino acid sequence of a viral protein linked to an immunoglobulin Fc region.

Protein derivatives may also be used as immunogens, reagents in receptor-based immunoassays, or as binding agents for affinity purification procedures of cytokines or other binding ligands. Vital protein derivatives may also be obtained by cross-linking agents, such as M-maleimidobenzoyl succinimide ester and N-hydroxysuccinimide, at cysteine and lysine residues. Proteins may also be covalently bound through reactive side groups to various insoluble substrates, such as cyanogen bromide-activated, bisoxirane-activated, carbonyldiimidazole-activated or tosyl-activated agarose structures, or by adsorbing to polyolefin surfaces (with or without glutaraldehyde cross-linking). Once bound to a substrate, proteins may be used to selectively bind (for purposes of assay or purification) antibodies raised against the vital protein or against cytokine receptors which are similar to the vital protein.

The vital proteins may exist as oligomers, such as dimers or trimers. Oligomers are linked by disulfide bonds formed between cysteine residues on different viral polypeptides. Alternatively, oligomers may be formed by constructing fusion proteins of viral proteins and the Fc region of an immunoglobulin molecule, such as human IgG1, to yield a fusion protein. The fusion proteins are allowed to assemble much like heavy chains of an antibody molecule to form divalent viral protein. If fusion proteins are made with both heavy and light chains of an antibody, it is possible to form a vital protein oligomer with as many as four viral protein regions. Alternative methods of preparing oligomers include the use of leucine zipper structures. A fusion protein comprising a viral protein and a leucine zipper will spontaneously form an oligomer in solution, as described in U.S Ser. No. 07/969,703, now pending the disclosure of which is incorporated by reference herein.

The present invention also includes viral proteins with or without associated native-pattern glycosylation. Proteins expressed in yeast or mammalian expression systems, e.g., COS-7 cells, may be similar or slightly different in molecular weight and glycosylation pattern than the native molecules, depending upon the expression system. Expression of viral DNAs in bacteria such as *E. coli* provides non-glycosylated molecules. Functional mutant analogs of viral protein having inactivated N-glycosylation sites can be produced by oligonucleotide synthesis and ligation or by site-specific mutagenesis techniques. These analog proteins can be produced in a homogeneous, reduced-carbohydrate form in good yield using yeast expression systems. N-glycosylation sites in eukaryotic proteins are characterized by the amino acid triplet Asn-$A_1$-Z, where $A_1$ is any amino acid except Pro, and Z is Set or Thr. In this sequence, asparagine provides a side chain amino group for covalent attachment of carbohydrate. Such a site can be eliminated by substituting another amino acid for Ash or for residue Z, deleting Asn or Z, or inserting a non-Z amino acid between $A_1$ and Z, or an amino acid other than Ash between Ash and $A_1$.

Viral protein derivatives may also be obtained by mutations of the native viral proteins or its subunits. A viral protein mutant, as referred to herein, is a polypeptide homologous to a viral protein but which has an amino acid sequence different from the native viral protein because of one or a plurality of deletions, insertions or substitutions.

Bioequivalent analogs of vital proteins may be constructed by, for example, making various substitutions of residues or sequences or deleting terminal or internal residues or sequences not needed for biological activity. For example, cysteine residues can be deleted or replaced with other amino acids to prevent formation of incorrect intramolecular disulfide bridges upon renaturation. Other approaches to mutagenesis involve modification of adjacent dibasic amino acid residues to enhance expression in yeast systems in which KEX2 protease activity is present. Generally, substitutions should be made conservatively; i.e., the most preferred substitute amino acids are those having physicochemical characteristics resembling those of the residue to be replaced. Similarly, when a deletion or insertion strategy is adopted, the potential effect of the deletion or insertion on biological activity should be considered. Subunits of viral proteins may be constructed by deleting terminal or internal residues or sequences.

Mutations in nucleotide sequences constructed for expression of analog viral proteins must, of course, preserve the reading frame phase of the coding sequences and preferably will not create complementary regions that could hybridize to produce secondary mRNA structures such as loops or hairpins which would adversely affect translation of the receptor mRNA. Although a mutation site may be predetermined, it is not necessary that the nature of the mutation per se be predetermined. For example, in order to select for optimum characteristics of routants at a given site, random mutagenesis may be conducted at the target codon and the expressed viral protein mutants screened for the desired activity.

Not all mutations in the nucleotide sequence which encodes a viral protein will be expressed in the final product, for example, nucleotide substitutions may be made to enhance expression, primarily to avoid secondary structure loops in the transcribed mRNA (see EPA 75,444A, incorporated herein by reference), or to provide codons that are more readily translated by the selected host, e.g., the well-known *E. coli* preference codons for *E. coli* expression.

Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques*, Jan. 1985, 12–19); Smith et al. (*Genetic Engineering: Principles and Methods*, Plenum Press, 1981); and U.S. Pat. Nos. 4,518,584 and 4,737,462 disclose suitable techniques, and are incorporated by reference herein.

Expression of Recombinant Vital Protein Cytokine Antagonists

The proteins of the present invention are preferably produced by recombinant DNA methods by inserting a DNA sequences encoding viral protein into a recombinant expression vector and expressing the DNA sequence in a recombinant microbial expression system under conditions promoting expression.

DNA sequences encoding the proteins provided by this invention can be assembled from cDNA fragments and short oligonucleotide linkers, or from a series of oligonucleotides, to provide a synthetic gene which is capable of being inserted in a recombinant expression vector and expressed in a recombinant transcriptional unit.

Recombinant expression vectors include synthetic or cDNA-derived DNA fragments encoding viral proteins or bioequivalent analogs operably linked to suitable transcriptional or translational regulatory elements derived from mammalian, microbial, vital or insect genes. Such regulatory elements include a transcriptional promoter, an optional operator sequence to control transcription, a sequence encoding suitable mRNA ribosomal binding sites, and sequences which control the termination of transcription and translation, Its described in detail below. The ability to replicate in a host, usually conferred by an origin of replication, and a selection gene to facilitate recognition of transformants may additionally be incorporated. DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading frame.

DNA sequences encoding vital proteins which are to be expressed in a microorganism will preferably contain no introns that could prematurely terminate transcription of DNA into mRNA. Due to code degeneracy, there can be considerable variation in nucleotide sequences encoding the same amino acid sequence. Other embodiments include sequences capable of hybridizing under moderately stringent conditions (prewashing solution of 5× SSC, 0.5% SDS, 1.0 mM EDTA {pH 8.0) and hybridization conditions of 50° C., 5× SSC, overnight) to the DNA sequences encoding vital proteins, and other sequences which are degenerate to those which encode the viral proteins.

Transformed host cells are cells which have been transformed or transfected with expression vectors constructed using recombinant DNA techniques and which contain sequences encoding the viral proteins of the present invention. Transformed host cells may express the desired viral protein, but host cells transformed for purposes of cloning or amplifying viral DNA do not need to express the vital protein. Expressed viral proteins will preferably be secreted into the culture supernatant, depending on the DNA selected, but may be deposited in the cell membrane. Suitable host cells for expression of viral proteins include prokaryotes, yeast or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed to produce vital proteins using RNAs derived from the DNA constructs disclosed herein. Appropriate cloning and expression vectors for use with bacterial, fungal, yeast, and mammalian cellular hosts are described by Pouwels et al. (*Cloning Vectors: A Laboratory Manual,* Elsevier, N.Y., 1985), the relevant disclosure of which is hereby incorporated by reference.

Prokaryotic expression hosts may be used for expression of viral proteins that do not require extensive proteolytic and disulfide processing. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Suitable prokaryotic hosts for transformation include *E. coli, Bacillus subtilis, Salmonella typhimurium,* and various species within the genera Pseudomonas, Streptomyces, and Staphylococcus, although others may also be employed as a matter of choice.

Useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed. *E. coli* is typically transformed using derivatives of pBR322, a plasmid derived from an *E. coli* species (Bolivar et al., *Gene* 2:95, 1977). pBR322 contains genes for ampicillin and tetracycline resistance and thus provides simple means for identifying transformed cells.

Promoters commonly used in recombinant microbial expression vectors include the $\beta$-lactamase (penicillinase) and lactose promoter system (Chang et al., *Nature* 275:615, 1978; and Goeddel et al., *Nature* 281:544, 1979), the tryptophan (trp) promoter system (Goeddel et al., *Nucl. Acids Res.* 8:4057, 1980; and EPA 36,776) and tac promoter (Maniatis, *Molecular Cloning: A Laboratory Manual,* Cold Spring Harbor Laboratory, p. 412, 1982). A particularly useful bacterial expression system employs the phage $\lambda$ $P_L$ promoter and cI857ts thermolabile repressor. Plasmid vectors available from the American Type Culture Collection which incorporate derivatives of the $\lambda$ $P_L$ promoter include plasmid pHUB2, resident in *E. coli* strain JMB9 (ATCC 37092) and pPLc28, resident in *E. coli* RR1 (ATCC 53082).

Recombinant viral proteins may also be expressed in yeast hosts, preferably from the Saccharomyces species, such as *S. cerevisiae.* Yeast of other genera, such as Pichia or Kluyveromyces may also be employed. Yeast vectors will generally contain an origin of replication from the 2$\mu$ yeast plasmid or an autonomously replicating sequence (ARS), promoter, DNA encoding the vital protein, sequences for polyadenylation and transcription termination and a selection gene. Preferably, yeast vectors will include an origin of replication and selectable marker permitting transformation of both yeast and *E. coli,* e.g., the ampicillin resistance gene of *E. coli* and *S. cerevisiae* trp1 gene, which provides a selection marker for a mutant strain of yeast lacking the ability to grow in tryptophan, and a promoter derived from a highly expressed yeast gene to induce transcription of a structural sequence downstream. The presence of the trp1 lesion in the yeast host cell genome then provides an effective environment for detecting transformation by growth in the absence of tryptophan.

Suitable promoter sequences in yeast vectors include the promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 7:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPA 73,657.

Preferred yeast vectors can be assembled using DNA sequences from pBR322 for selection and replication in *E. coli* ($Amp^r$ gene and origin of replication t and yeast DNA sequences including a glucose-repressible ADH2 promoter and $\alpha$-factor secretion leader. The ADH2 promoter has been described by Russell et al. (*J. Biol. Chem.* 258:2674, 1982) and Beier et al. (*Nature* 300:724, 1982). The yeast $\alpha$-factor leader, which directs secretion of heterologous proteins, can be inserted between the promoter and the structural gene to be expressed. See, e.g., Kurjan et al., *Cell* 30:933, 1982; and Bitter et al., *Proc. Natl. Acad. Sci. USA* 81:5330, 1984. The leader sequence may be modified to contain, near its 3′ end, one or more useful restriction sites to facilitate fusion of the leader sequence to foreign genes.

Suitable yeast transformation protocols are known to those of skill in the art: an exemplary technique is described by Hinnen et al., *Proc. Natl. Acad. Sci. USA* 75:

1929, 1978, selecting for $Trp^+$ transformants in a selective medium consisting of 0.67% yeast nitrogen base, 0.5% casamino acids, 2% glucose, 10 μg/ml adenine and 20 μg/ml uracil.

Host strains transformed by vectors comprising the ADH2 promoter may be grown for expression in a rich medium consisting of 1% yeast extract, 2% peptone, and 1% glucose supplemented with 80 μg/ml adeninc and 80 μg/ml uracil. Derepression of the ADH2 promoter occurs upon exhaustion of medium glucose. Crude yeast supernatants are harvested by filtration and held at 4° C. prior to further purification.

Various mammalian or insect cell culture systems can be employed to express recombinant protein. Baculovirus systems for production of heterologous proteins in insect cells are reviewed by Luckow and Summers, *Bio/Technology* 6:47 (1988). Examples of suitable mammalian host cell lines include the COS-7 lines of monkey kidney cells, described by Gluzman (*Cell* 23: 175, 1981), and other cell lines capable of expressing an appropriate vector including, for example, CV-1/EBNA (ATCC CRL 10478), L cells, C127, 3T3, Chinese hamslet ovary (CHO), HeLa and BHK cell lines. Mammalian expression vectors may comprise nontranscribed elements such as an origin of replication, a suitable promoter and enhancer linked to the gene to be expressed, and other 5′ or 3′ flanking nontranscribed sequences, and 5′ or 3′ nontranslated sequences, such as necessary ribosome binding sites, a polyadenylation site, splice donor and acceptor sites, and transcriptional termination sequences.

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al., *Nature* 273:113, 1978). Smaller or larger SV40 fragments may also be used, provided the approximately 250 bp sequence extending from the Hind III site toward the BglI site located in the viral origin of replication is included. Further, vital genomic promoter, control and/or signal sequences may be utilized, provided such control sequences are compatible with the host cell chosen. Exemplary vectors can be constructed as disclosed by Okayarea and Berg (*Mol. Cell. Biol.* 3:280, 1983).

A useful system for stable high level expression of mammalian receptor cDNAs in C127 murine mammary epithelial cells can be constructed substantially as described by Cosman et al. (*Mol. Immunol.* 23:935, 1986).

A particularly preferred eukaryotic vector for expression of viral protein DNA is disclosed below in Example 2. This vector, referred to as pDC406 (McMahan et al., *EMBO J.* 10:2821, 1991), includes regulatory sequences derived from SV40, human immunodeficiency virus (HIV), and Epstein-Bart virus (EBV). A useful cell line that allows for episomal replication of expression vectors, such as pDC406, that contain the EBV origin of replication is CV-1/EBNA (ATCC CRL 10478). The CV-1/EBNA cell line was derived by transfection of the CV- 1 cell line with a gene encoding Epstein-Barr virus nuclear antigen-1 (EBNA-1) and constitutively express EBNA-1 driven from human CMV immediate-early enhancer/promoter.

Purified vital proteins or analogs are prepared by culturing suitable host/vector systems to express the recombinant translation products of the DNAs of the present invention, which are then purified from culture media or cell extracts.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. For example, a suitable affinity matrix can comprise a viral protein or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred.

Finally, one or more reversed-phase high performance liquid chromatography (RP-HPLC) steps employing hydrophobic RP-HPLC media, e.g., silica gel having pendant methyl or other aliphatic groups, can be employed to further purify a viral protein composition. Some or all of the foregoing purification steps, in various combinations, can also be employed to provide a homogeneous recombinant protein.

Recombinant vital protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant viral protein can be disrupted by any convenient method, including freeze-thaw cycling, sonication, mechanical disruption, or use of cell lysing agents.

Fermentation of yeast which express viral protein as a secreted protein greatly simplifies purification. Secreted recombinant protein resulting from a large-scale fermentation can be purified by methods analogous to those disclosed by Urdal et al. (*J. Chromatog.* 296:171, 1984). This reference describes two sequential, reversed-phase HPLC steps for purification of recombinant human GM-CSF on a preparative HPLC column.

Viral protein synthesized in recombinant culture is characterized by the presence of non-viral cell components, including proteins, in amounts and of a character which depend upon the purification steps taken to recover the vital protein from the culture. These components ordinarily will be of yeast, prokaryotic or non-human higher eukaryotic origin and preferably are present in innocuous contaminant quantities, on the order of less than about 1 percent by weight. Further, recombinant cell culture enables the production of viral protein free of other proteins which may be normally associated with the viral protein as it is found in nature in its species of origin, e.g. in cells, cell exudates or body fluids.

Administration of Vital Protein Compositions

The present invention provides methods of using therapeutic compositions comprising an effective amount of a vital protein and a suitable diluent and carrier, and methods for regulating an immune response. The use of A53R-equivalent proteins in conjunction with soluble cytokine receptors, e.g., TNF receptor, is also contemplated.

For therapeutic use, purified viral protein is administered to a patient, preferably a human, for treatment in a manner appropriate to the indication. Thus, for example, A53R-equivalent protein compositions administered to suppress immune function can be given by bolus injection, continuous infusion, sustained release from implants, or other suitable technique. Typically, a therapeutic agent will be administered in the form of a composition comprising purified protein in conjunction with physiologically acceptable carriers, excipients or diluents. Such carriers will be nontoxic to recipients at the dosages and concentrations employed. Ordinarily, the preparation of such compositions entails combining the vital protein with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with conspecific serum albumin are exemplary appropriate diluents. Preferably, product is formulated as a lyophilizate using appropriate excipient solutions (e.g., sucrose) as diluents. Appropriate dosages can be determined in trials. The amount and frequency of administration will depend, of course, on such factors as the nature and severity of the indication being treated, the desired response, the condition of the patient, and so forth.

A53R-equivalent proteins are administered for the purpose of inhibiting TNF dependent responses. TNF is used clinically as an antitumor agent and results in severe toxicities. The toxicities associated with the administration of TNF are identical to the effects that the cytokine manifests when it is produced in normal or overactive immune responses. It is believed that TNF produced as a result of the immune response to malignant tissue is a causative factor of cachexia. In addition, TNF is produced in the course of other immune reactions such as the body's response to severe bacterial infection where TNF production can contribute to the development of septic shock. The production of other key cytokines (IL-1, IL-2 or a number of colony stimulating factors) can also induce significant host production of TNF. Thus, the side effects of these cytokines at certain doses administered to human patients have been attributed to the induction of TNF production. Because TNF binds to a specific TNF receptor present on the surface of responsive cells, viral TNF antagonists, such as A53R-equivalent protein, may be useful as a therapy for cachexia or septic shock or to treat side effects associated with cytokine therapy.

The following examples are offered by way of illustration, and not by way of limitation.

EXAMPLE 1

Binding Assays

A. Radiolabeling of TNFα and TNFβ. Radiolabeled. TNFα and TNFβ (used in various assays for TNF antagonists) are derived as follows. Recombinant human TNFα, in the form of a fusion protein containing a hydrophilic octapeptide at the N-terminus, is expressed in yeast as a secreted protein and purified by affinity chromatography (Hopp et al., *Bio/Technology* 6:1204, 1988). Purified recombinant human TNFβ is purchased from R&D Systems (Minneapolis, Minn.). Both proteins are radiolabeled to a specific activity of about $2\times10^{15}$ cpm/mmole using the commercially available solid phase agent, Iodogen (Pierce). In this procedure, 5 μg of Iodogen is plated at the bottom of a 10×75 mm glass tube and incubated for 20 minutes at 4° C. with 75 μl of 0.1M sodium phosphate, pH 7.4 and 20 μl (2 mCi) Na $^{125}$I. This solution is then transferred to a second glass tube containing 5 μg TNFα (or TNF-β) in 45 μl PBS for 20 minutes at 4° C. The reaction mixture is fractionareal by gel filtration on a 2 ml bed volume of Sephadex G-25 (Sigma) equilibrated in Roswell Park Memorial Institute (RPMI) 1640 medium containing 2.5% (w/v) bovine serum albumin (BSA), 0.2% (w/v) sodium azide and 20 mM Hepes pH 7.4 (binding medium). The final pool of $^{125}$I-TNF is diluted to a working stock solution of about $1\times10^{-7}$M in binding medium and stored for up to 3 weeks at 4° C. without significant loss of receptor binding activity.

B. Detection of A53R-Equivalent Binding to TNF. Two separate binding assays are used to measure A53R-Equivalent protein binding to TNF. In the first method, the presence of a fusion protein comprising cowpox A53R-equivalent protein fused to a human IgG Fc region (referred to as A53R-Fc) in COS-7 cell supernatants is measured by inhibition of $^{125}$I-TNFα binding to U937 cells. Supernatants from COS cells transfected with recombinant A53R-Fc constructs are harvested three days post-transfection. Serial two-fold dilutions of supernatants are pre-incubated with 0.3 nM $^{125}$I-TNFα (specific activity $1\times10^{15}$ cpm/mmole) for two hours at 4° C. prior to the addition of $2\times10^{6}$ U937 cells. The cells are incubated for an additional two hours at 4° C., after which free and cell bound human $^{125}$I-TNFα are separated using a pthalate oil separation method (Dower et al., *J. Immunol.* 132:751, 1984) essentially as described by Park et al. (*J. Biol. Chem.* 261:4177, 1986). Non-specific ligand binding in all assays is determined by the inclusion of a 200 molar excess of unlabeled ligand.

In the second method, $^{125}$I-TNF binding to A53R-Fc protein is detected directly by nitrocellulose dot blots. The ability of TNF receptor or A53R-Fc to be stably adsorbed to nitrocellulose from detergent extracts of human cells yet retain binding activity provided a means of detecting A53R-Fc. Cell extracts are prepared by mixing a cell pellet with a 2× volume of PBS containing 1% Triton X-100 and a cocktail of protease inhibitors (2 mM phenylmethyl sulfonyl fluoride, 10 μM pepstatin, 10 μM leupeptin, 2 mM o-phenanthroline and 2 mM EGTA) by vigorous vortexing. The mixture is incubated on ice for 30 minutes after which it is centrifuged at 12,000× g for 15 minutes at 8° C. to remove nuclei and other debris. Alternatively, recombinant A53R-Fc protein in the form of COS supernatants are mixed with an equal volume of PBS/1% Triton X-100 and a cocktail of the same protease inhibitors. Two microliter aliquots of cell extracts or A53R-Fc protein extracts are placed on dry BA85/21 nitrocellulose membranes (Schleicher and Schuell, Keene, N.H.) and allowed to dry. The membranes are incubated in tissue culture dishes for 4 hours in Tris (0.05M) buffered saline (0.15M) pH 7.5 containing 3% w/v BSA to block nonspecific binding sites. The membrane is then covered with $5\times10^{-11}$M $^{125}$I-TNF in PBS+3% BSA and incubated for 2 hr at 4° C. with shaking. At the end of this time, the membranes are washed 3 times in ice-cold PBS, dried and placed on Kodak X-Omat AR film for 18 hr at −70° C.

EXAMPLE 2

Isolation and Expression of the Cowpox A53R-Equivalent ORF

A plasmid (p1464) containing the Cowpox Virus A53R-Equivalent opening reading frame (CPV A53R-Equivalent ORF; a Psi I/Cla I fragment of CPV that corresponds to the A53R locus of vaccinia) cloned into Nsi I/Cla I cut pGEM72F vector (Promega, Madison, Wis.) was obtained from Dr. David Pickup of Duke University, Durham, N.C. The plasmid was partially sequenced by Dr. Pickup, to confirm that it contained the A53R-Equivalent locus. Subsequent sequencing of the entire plasmid was conducted to determine the location of that region that encoded a protein likely to bind TNF, and to prepare appropriate oligonucleotides to utilize as probes in polymerase chain reaction (PCR) for cloning the TNF-binding portion from the plasmid.

PCR conditions were as follows: five cycles of 94° C., one minute: 50° C., one minute; 72° C., one minute; 20 cycles of 94° C., one minute, 60° C., one minute, 72° C., one minute; and one cycle of 72° C., 5 minutes. The oligonucleotides used were:

Spe I A53R-Equivalent (SEQ ID NO: 1)
5'-CGCACTAGTTCTGATATACCTACTTCGTCACTGCCA

A53R-Equivalent Fc Bgl II (SEQ ID NO: 2)
3'-GGTACGTTTGATGATAGATTTACATTACTCGGGTCTAGACGC Not I A53R-Equivalent (SEQ ID NO: 3)
5'-ATAGCGGCCGCCACCATGGATATAAAGAAATTTGCTGACT A53R-Equivalent Bgl II (SEQ ID NO: 4)
3'-GGTACGTTTGATGATAGATTTACATTAATCTCTAGACGC The oligonucleotide defined by SEQ D NO:1 deletes the first 21 amino acids of the CPV A53R-Equivalent protein; these are subsequently replaced with the murine IL-7 leader sequence (U.S. Pat. No. 4,965,195). The oligonucleotide defined by SEQ ID NO:2 represents the oligonucleotide for the 3' end of the portion of CPV A53R-Equivalent that was believed to encode a TNF-binding protein. A six-nucleotide long segment was included between the CPV A53R-Equivalent fragment and the Bgl II site, to allow a three-way ligation with DNA encoding a human IgG Fc. The oligonucleofide defined by SEQ ID NO:3 represents the CPV A53R-Equivalent locus with the viral leader sequence intact. The oligonucleotide defined by SEQ ID NO:4 represents the same segment as described for SEQ D NO:2, without the six-nucleotide long segment complementary to a human IgG Fc.

PCR products were purified by agarose gel electrophoresis. The appropriate bands were cut from the gel, and the amplified nucleotide sequences were eluted. For the fragment obtained by using SEQ ID NOs: 1 and 2, the purified PCR product was cut with Spe I/Bgl II, and cloned into a Spe I-cleaved SMAG vector, a derivative of pDC201 (Sims et al., *Science* 241:585, 1988) that contains the murine IL-7 leader sequence, in a three-way ligation that included a Bgl II/Not I fragment of a DNA encoding a human IgG Fc region (described in U.S. Ser. No. 07/969,703). The resulting DNA construct, referred to as A53R/SMAG, was transfected into COS-7 cells. In COS-7 cells, the A53R-Equivalent fusion protein is expressed off of the adenovirus-2 promotor. For the fragment obtained by using SEQ ID NOs:3 and 4, the purified material was cut with Not I/Bgl II, and cloned into HAVEO (pDC406; McMahan et al., *EMBO J.* 10:2821, 1991) which had been cut with Not I and de-phosphorylated with calf intestinal alkaline phosphatase (CIAP), in a three-way ligation that included a Bgl II/Not I fragment of a human IgG Fc region. The resulting DNA construct, referred to as wtA53R/HAVEO, was transfected into CV-1/EBNA cells (ATCC CRL 10478). In such cells, the A53R-Equivalent fusion protein is is expressed off of the HIV-1 promotor.

EXAMPLE 3

Purification of CPV A53R-Equivalent Protein by TNF Affinity Chromatography

CPV A53R-Equivalent protein is purified from cell supernatants of Example 2 using TNF as an affinity ligand. To obtain large amounts of recombinant TNF for preparation of a TNF affinity matrix, a Flag®-TNF fusion protein containing the "Flag®" octapeptide Asp-Tyr-Lys-Asp-Asp-Asp-Asp-Lys (SEQ ID NO:7) fused to the amino terminus of TNF is constructed and expressed. This octapeptide sequence does not alter the biological activity of TNF, is highly antigenic and provides an epitope reversibly bound by a specific monoclonal antibody, enabling facile purification of the expressed TNF (Hopp et al., *Bio/Technology* 6:1204 (1988).

The Flag®-TNF fusion protein is coupled to Affi-gel-10 (Bio-Rad) or CnBr-activated Sepharose 4B (Pharmacia LKB Biotechnology, Inc.) according to the manufacturer's suggestions and as previously described by Urdal et al., *J. Biol. Chem.* 263:2870 (1988). Conditioned medium from Example 2 is harvested and centrifuged and the resulting conditioned medium (RPMI 1640) is adjusted to 1% BSA, 0.1% sodium azide, 20 mM HEPES, pH 7.4. To the conditioned medium is added a cocktail of protease inhibitors (2 mM PMSF, 2 mM O-phenanthroline, 1 mM pepstatin, 1 mM leupeptin). The resulting medium is applied to a Flag®-TNF affinity column equilibrated with PBS, pH 7.4. The column is then washed with 10 column volumes of PBS, pH 7.4, after which bound protein is eluted with 0.1M glycine-HCl, pH 3.0. Eluate containing CPV A53R-Equivalent protein is immediately neutralized with 80 ml of 1.0M HEPES, pH 7.4 and aliquots removed for binding assays (described in Example 1, above) and analysis by SDS-PAGE as previously described by Urdal, *J. Biol. Chem.* 263:2870 (1988).

EXAMPLE 4

Purification of CPV A53R-Equivalent Protein Using Reversed-Phase HPLC

CPV A53R-Equivalent protein is also purified by conventional methods using Flag ®-TNF binding as a biological assay for detection of CPV A53R-Equivalent activity. Flag ®-TNF is produced as described in Example 3 above. Conditioned medium from Example 2 is harvested and centrifuged and the resulting conditioned medium (RPMI 1640) is adjusted to 1% BSA, 0.1% sodium azide, 0.5M $CaCl_2$ and 20 mM HEPES, pit 7.4. To the conditioned medium is added a cocktail of protease inhibitors (2 mM PMSF, 2 mM O-phenanthroline, 1 mM pepstalin, 1 mM leupeptin). CPV A53R-Equivalent protein is purified from the resulting medium by conventional purification methods, including ion-exchange, hydrophobic interaction, gel exclusion and reversed-phase HPLC.

EXAMPLE 5

Purification of CPV A53R-Equivalent/Fc Fusion Protein by Protein A/G Chromatography CPV A53R-Equivalent/Fc fusion protein is purified by conventional methods using Protein A or Protein G chromatography. Approximately one liter of culture supernatant containing A53R-Equivalent/Fc fusion protein is purified by filtering mammalian cell supernatants (e.g., in a 0.45 m filter) and applying flitrate to a protein A/G antibody affinity column (Schleicher and Schuell, Keene, N.H.) at 4° C. at a flow rate of 80 ml/hr for a 1.5 cm×12.0 cm column. The column is washed with 0.5M NaCl in PBS until free protein is not detected in the wash buffer. Finally, the column is washed with PBS. Bound fusion protein is eluted from the column with 25 mM citrate buffer, pH 2.8, and brought to pH 7 with 500 mM Hepes buffer, pH 9.1. Flag ®-TNF binding is used as a biological assay for detection of CPV A53R-Equivalent activity. Flag ®-TNF is produced as described in Example 3 above.

EXAMPLE 6

Preparation of Monoclonal Antibodies to CPV A53R-Equivalent Protein

Preparations of purified recombinant CPV A53R-Equivalent, for example, or transfected cells expressing high levels of CPV A53R-Equivalent, are employed to generate monoclonal antibodies against CPV A53R-Equivalent using conventional techniques, for example, those disclosed in U.S. Pat. No. 4,411,993. Such antibodies are likely to be useful in interfering with TNF binding to TNF receptors, for example, in ameliorating toxic or other undesired effects of TNF, or as components of diagnostic or research assays for TNF or soluble TNF receptor.

To immunize mice, CPV A53R-Equivalent immunogen is emulsified in complete Freund's adjuvant and injected in amounts ranging from 10–100 μg subcutaneously into Balb/c mice. Ten to twelve days later, the immunized animals are boosted with additional immunogen emulsified in incomplete Freund's adjuvant and periodically boosted thereafter on a weekly to biweekly immunization schedule. Serum samples are periodically taken by retro-orbital bleeding or tail-tip excision for testing by dot-blot assay (antibody sandwich) or ELISA (enzyme-linked immunosorbent assay). Other assay procedures are also suitable. Following detection of an appropriate antibody liter, positive animals are given an intravenous injection of antigen in saline. Three to four days later, the animals are sacrificed, splenocytes harvested, and fused to a murine myeloma cell line (e.g., NS1 or preferably Ag 8.653 IATCC CRL 1580]). Hybridoma cell lines generated by this procedure are plated in multiple microtiter plates in a HAT selective medium (hypoxanthine, aminopterin, and thymidine) to inhibit proliferation of non-fused cells, myeloma hybrids, and spleen cell hybrids.

Hybridoma clones thus generated can be screened by ELISA for reactivity with CPV A53R-Equivalent or TNF receptor, for example, by adaptations of the techniques disclosed by Engvall et al., *Immunochem.* 8:871 (1971) and in U.S. Pat. No. 4,703,004. A preferred screening technique is the antibody capture technique described by Beckman et al., *J. Immunol.* 144:4212 (1990). Positive clones are then injected into the peritoneal cavities of syngeneic Balb/c mice to produce ascites containing high concentrations (>1 mg/ml) of anti-CPV A53R-Equivalent monoclonal antibody. The resulting monoclonal antibody can be purified by ammonium sulfate precipitation followed by gel exclusion chromatography. Alternatively, affinity chromatography based upon binding of antibody to protein A or protein G can also be used, as can affinity chromatography based upon binding to A53R-Equivalent protein.

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:

-continued ( B ) CLONE: Oligo1

( x i ) SEQUENCE DESCRIPTION: SEQ ID NO:1:

CGCACTAGTT CTGATATACC TACTTCGTCA CTGCCA 36

( 2 ) INFORMATION FOR SEQ ID NO:2:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: YES ( v i i ) IMMEDIATE SOURCE:
( B ) CLONE: Oligo 2

( x i ) SEQUENCE DESCRIPTION: SEQ ID NO:2:

CGCAGATCTG GGCTCATTAC ATTTAGATAG TAGTTTGCAT GG 42

( 2 ) INFORMATION FOR SEQ ID NO:3:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:
( B ) CLONE: Oligo 3

( x i ) SEQUENCE DESCRIPTION: SEQ ID NO:3:

ATAGCGGCCG CCACCATGGA TATAAAGAAA TTTGCTGACT 40

( 2 ) INFORMATION FOR SEQ ID NO:4:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: YES ( v i i ) IMMEDIATE SOURCE:
( B ) CLONE: Oligo 4

( x i ) SEQUENCE DESCRIPTION: SEQ ID NO:4:

CGCACATCTC TAATTACATT TAGATAGTAG TTTGCATGG 39

( 2 ) INFORMATION FOR SEQ ID NO:5:

( i ) SEQUENCE CHARACTERISTICS:
( A ) LENGTH: 561 base pairs
( B ) TYPE: nucleic acid
( C ) STRANDEDNESS: single
( D ) TOPOLOGY: linear ( i i ) MOLECULE TYPE: cDNA -continued ( i i i ) HYPOTHETICAL: NO ( i v ) ANTI-SENSE: NO ( v i ) ORIGINAL SOURCE:
( A ) ORGANISM: Cowpox Virus ( v i i ) IMMEDIATE SOURCE:
( B ) CLONE: A53R-Eqivalent ( i x ) FEATURE:
( A ) NAME/KEY: CDS
( B ) LOCATION: 1..561

( x i ) SEQUENCE DESCRIPTION: SEQ ID NO:5:

```
ATG GAT ATA AAG AAT TTG CTG ACT GTA TGT ACT ATT TTG TAC ATC AGT     48
Met Asp Ile Lys Asn Leu Leu Thr Val Cys Thr Ile Leu Tyr Ile Ser
  1               5                  10                  15

ACA TTG GTT ACA GCA GAT ATA CCT ACT TCG TCA CTG CCA CAC GCT CCG     96
Thr Leu Val Thr Ala Asp Ile Pro Thr Ser Ser Leu Pro His Ala Pro
             20                  25                  30

GTA AAC GGG TCA TGT GAC GAC GGA GAA TAT CTT GAT AAG ACG CAT AAT    144
Val Asn Gly Ser Cys Asp Asp Gly Glu Tyr Leu Asp Lys Thr His Asn
         35                  40                  45

CAA TGT TGT AAT CGG TGT CCA CCT GGA GAA TTT GCC AAG ATC AGA TGT    192
Gln Cys Cys Asn Arg Cys Pro Pro Gly Glu Phe Ala Lys Ile Arg Cys
     50                  55                  60

AGC GGT AGC GAT AAC ACA AAA TGT GAA CGC TGC CCA CCT CAT ACA TAT    240
Ser Gly Ser Asp Asn Thr Lys Cys Glu Arg Cys Pro Pro His Thr Tyr
 65                  70                  75                  80

ACC ACA GTA CCC AAT TAT TCT AAT GGA TGT CAT CAA TGT AGG AAA TGC    288
Thr Thr Val Pro Asn Tyr Ser Asn Gly Cys His Gln Cys Arg Lys Cys
                 85                  90                  95

CCA ACA GGA TCA TTT GAT AAG GTA AAG TGT ACC GGA ACA CAG AAC AGT    336
Pro Thr Gly Ser Phe Asp Lys Val Lys Cys Thr Gly Thr Gln Asn Ser
            100                 105                 110

AAA TGT TCG TGT CTT CCT GGT TGG TTT TGC GCT ACT GAT TCT TCG AAG    384
Lys Cys Ser Cys Leu Pro Gly Trp Phe Cys Ala Thr Asp Ser Ser Lys
        115                 120                 125

ACT GAA GAT TGT CGA GAT TGT ATA CCA AAA AGA AAA TGT CCA TGT GGA    432
Thr Glu Asp Cys Arg Asp Cys Ile Pro Lys Arg Lys Cys Pro Cys Gly
    130                 135                 140

TAC TTT GGT GGA ATA GAT GAA CTC GGA AAT CCT CTT TGT AAA TCG TGT    480
Tyr Phe Gly Gly Ile Asp Glu Leu Gly Asn Pro Leu Cys Lys Ser Cys
145                 150                 155                 160

TGT GTT GGT GAA TAT TGC GAC GAC ATA CGT AAT CAT AGA GTT GGT CCT    528
Cys Val Gly Glu Tyr Cys Asp Asp Ile Arg Asn His Arg Val Gly Pro
                165                 170                 175

TTT CCT CCA TGC AAA CTA TCT AAA TGT AAT TAG                        561
Phe Pro Pro Cys Lys Leu Ser Lys Cys Asn
            180                 185
```

( 2 ) INFORMATION FOR SEQ ID NO:6:

( i ) SEQUENCE CHARACTERISTICS:
( A ) LENGTH: 186 amino acids
( B ) TYPE: amino acid
( D ) TOPOLOGY: linear ( i i ) MOLECULE TYPE: protein ( x i ) SEQUENCE DESCRIPTION: SEQ ID NO:6:

```
Met Asp Ile Lys Asn Leu Leu Thr Val Cys Thr Ile Leu Tyr Ile Ser
  1               5                  10                  15

Thr Leu Val Thr Ala Asp Ile Pro Thr Ser Ser Leu Pro His Ala Pro
             20                  25                  30
```

-continued

| | | | | | | | | | | | | | | | |
|---|---|---|---|---|---|---|---|---|---|---|---|---|---|---|---|
| Val | Asn | Gly<br>35 | Ser | Cys | Asp | Asp | Gly<br>40 | Glu | Tyr | Leu | Asp | Lys<br>45 | Thr | His | Asn |
| Gln | Cys<br>50 | Cys | Asn | Arg | Cys | Pro<br>55 | Pro | Gly | Glu | Phe | Ala<br>60 | Lys | Ile | Arg | Cys |
| Ser<br>65 | Gly | Ser | Asp | Asn | Thr<br>70 | Lys | Cys | Glu | Arg | Cys<br>75 | Pro | Pro | His | Thr | Tyr<br>80 |
| Thr | Thr | Val | Pro | Asn<br>85 | Tyr | Ser | Asn | Gly | Cys<br>90 | His | Gln | Cys | Arg | Lys<br>95 | Cys |
| Pro | Thr | Gly | Ser<br>100 | Phe | Asp | Lys | Val | Lys<br>105 | Cys | Thr | Gly | Thr | Gln<br>110 | Asn | Ser |
| Lys | Cys | Ser<br>115 | Cys | Leu | Pro | Gly | Trp<br>120 | Phe | Cys | Ala | Thr | Asp<br>125 | Ser | Ser | Lys |
| Thr | Glu<br>130 | Asp | Cys | Arg | Asp | Cys<br>135 | Ile | Pro | Lys | Arg | Lys<br>140 | Cys | Pro | Cys | Gly |
| Tyr<br>145 | Phe | Gly | Gly | Ile | Asp<br>150 | Glu | Leu | Gly | Asn | Pro<br>155 | Leu | Cys | Lys | Ser | Cys<br>160 |
| Cys | Val | Gly | Glu | Tyr<br>165 | Cys | Asp | Asp | Ile | Arg<br>170 | Asn | His | Arg | Val | Gly<br>175 | Pro |
| Phe | Pro | Pro | Cys<br>180 | Lys | Leu | Ser | Lys | Cys<br>185 | Asn | | | | | | |

( 2 ) INFORMATION FOR SEQ ID NO:7:

( i ) SEQUENCE CHARACTERISTICS:
( A ) LENGTH: 8 amino acids
( B ) TYPE: amino acid
( D ) TOPOLOGY: linear ( i i ) MOLECULE TYPE: peptide ( x i ) SEQUENCE DESCRIPTION: SEQ ID NO:7:

| | | | | | | | |
|---|---|---|---|---|---|---|---|
| Asp<br>1 | Tyr | Lys | Asp | Asp<br>5 | Asp | Asp | Lys |

We claim:

1. An isolated and substantially homogeneous soluble viral protein encoded by an open reading frame present in a Pst I/Cla I fragment of cowpox virus, wherein the viral protein comprises the sequence of amino acids 1 through 186 of SEQ ID NO:6.

2. An isolated and substantially homogeneous soluble poxvirus protein which binds Tumor Necrosis Factor (TNF), wherein the DNA encoding the poxvirus protein hybridizes to the complementary strand of SEQ ID NO:5, nucleotides 1 through 561, under stringent conditions.

* * * * *

UNITED STATES PATENT AND TRADEMARK OFFICE
CERTIFICATE OF CORRECTION

PATENT NO. : 5,359,039
DATED : October 25, 1994
INVENTOR(S) : Craig A. Smith, et al It is certified that error appears in the above-indentified patent and that said Letters Patent is hereby corrected as shown below:

Column 3, line 3, remove "contains" and replace with -- contain --.
Column 3, lines 20 and 23, remove "vital" and replace with -- viral --.
Column 6, line 6, remove "n-my" and replace with -- may --.
Column 6, lines 58 and 59, remove "vital" and replace with -- viral --.
Column 7, line 26, remove "Set" and replace with -- Ser --.
Column 7, lines 29 and 32, remove "Ash" and replace with -- Asn --.
Column 8, line 1, remove "routants" and replace with -- mutants --.
Column 8, line 57, remove "Its" and replace with -- as --.
Column 9, line 13, remove "{" and replace with -- ( --.
Column 9, lines 25 and 35, remove "vital" and replace with -- viral --.
Column 10, line 53, remove "t" and replace with -- ) --.
Column 11, line 22, remove "hamslet" and replace with -- hamster --.
Column 12, lines 5, 37, and 60, remove "vital" and replace with -- viral --.
Column 13, lines 1, 3, and 23, remove "vital" and replace with -- viral --.
Column 13, line 65, remove "." after the word Radiolabeled.
Column 14, line 16, remove "fractionareal" and replace with --fractionated--

UNITED STATES PATENT AND TRADEMARK OFFICE

CERTIFICATE OF CORRECTION

PATENT NO. : 5,359,039

DATED : October 25, 1994

INVENTOR(S) : Craig A. Smith, et al

It is certified that error appears in the above-indentified patent and that said Letters Patent is hereby corrected as shown below:

Column 17, line 12, remove "pit" and replace with -- pH --.
Column 17, line 15, remove "pepstalin" and replace with -- pepstatin --.
Column 17, line 30, remove "flitrate" and replace with -- filtrate --.
Column 18, line 25, remove "I" and replace with -- [ -- before the abbreviation ATCC.

Signed and Sealed this

Second Day of July, 1996

Attest:

BRUCE LEHMAN

*Attesting Officer*

*Commissioner of Patents and Trademarks*